United States Patent [19]

Arganbright et al.

[11] Patent Number: 5,231,234
[45] Date of Patent: Jul. 27, 1993

[54] TWO STAGE PRODUCTION OF ETHER FROM TERTIARY ALCOHOL

[75] Inventors: Robert P. Arganbright; Bradley S. Hearn, both of Houston, Tex.

[73] Assignee: Chemical Research & Licensing Company, Pasadena, Tex.

[21] Appl. No.: 860,174

[22] Filed: Mar. 30, 1992

[51] Int. Cl.$^5$ ............................................. C07K 41/06
[52] U.S. Cl. ...................................... 568/697; 585/139
[58] Field of Search .......................... 568/697; 585/634

[56] References Cited

U.S. PATENT DOCUMENTS

| | | | |
|---|---|---|---|
| 3,256,250 | 6/1966 | Frilette | 568/895 |
| 3,267,156 | 8/1966 | Hansen | 260/614 |
| 3,510,538 | 5/1970 | Rosenthal | 585/639 |
| 4,039,590 | 8/1977 | Ancillotti | 260/614 |
| 4,198,530 | 4/1980 | Wentzheimer | 568/697 |
| 4,215,011 | 7/1980 | Smith | 252/426 |
| 4,232,177 | 11/1980 | Smith | 585/324 |
| 4,242,530 | 12/1980 | Smith | 585/510 |
| 4,302,356 | 11/1981 | Smith | 252/426 |
| 4,307,254 | 12/1981 | Smith | 568/697 |
| 4,336,407 | 6/1982 | Smith | 568/697 |
| 4,423,251 | 12/1983 | Pujado et al. | 568/697 |
| 4,439,350 | 3/1984 | Jones | 502/527 |
| 4,443,559 | 4/1984 | Smith | 502/527 |
| 4,447,668 | 5/1984 | Smith | 585/639 |
| 4,482,775 | 11/1984 | Smith | 585/671 |
| 4,827,048 | 5/1989 | Knifton | 568/698 |
| 4,918,244 | 4/1990 | Nelson | 568/698 |
| 5,118,873 | 6/1992 | Smith | 568/697 |

FOREIGN PATENT DOCUMENTS 2123411 2/1984 United Kingdom ................ 568/647

Primary Examiner—Howard T. Mars
Attorney, Agent, or Firm—Kenneth H. Johnson

[57] ABSTRACT

An integrated two stage process for the production of isoolefin by the dehydration of isoalcohol and the synthesis of a corresponding ether, for example the production of methyl tertiary butyl ether by (a) feeding tertiary butyl alcohol to a first distillation column reactor into a feed zone; (b) concurrently in said first distillation column reactor (i) contacting said TBA with an acid ion exchange resin catalyst as a component of a distillation structure, at a temperature in the range of 165° to 200° F. to dissociate said tertiary butyl alcohol to the isobutene and water, characterized in that sufficient water is maintained in said distillation reaction zone to inhibit the reaction of the isobutene with itself to form dimers and (ii) separating isobutene and water by fractional distillation; (c) withdrawing isobutene as overheads; (d) withdrawing water and undehydrated isoalcohol as bottoms, and in the second stage feeding the recovered isobutene to a second distillation column reactor with methanol and concurrently reacting methanol and isobutene at the appropriate dilution to form a reaction mixture containing methyl tertiary butyl ether.

16 Claims, 1 Drawing Sheet

TWO STAGE PRODUCTION OF ETHER FROM TERTIARY ALCOHOL

BACKGROUND OF THE INVENTION

1. Field of the Invention

The present invention relates to an integrated process for the production of isoolefin by the dehydration of isoalcohol and the synthesis of a corresponding ether. More particularly the invention relates to the first stage concurrent dehydration of tertiary butyl alcohol, recovery of isobutene and the second stage concurrent etherification of the recovered isobutene with an alcohol and recovery of ether.

2. Related Art

Methyl tertiary butyl ether (MTBE) is a useful component for improving the octane of gasolines and has commonly been prepared by the acid catalyzed reaction of methanol with isobutene. Examples of such a process are disclosed in U.S. Pat. Nos. 4,039,590 and 4,198,530.

Recently a new method of carrying out catalytic reactions has been developed, wherein the components of the reaction system are concurrently separable by distillation, using the catalyst structures as the distillation structures. This method is now generally known as catalytic distillation and any reference to catalytic distillation herein will be taken to mean this method or process. Such systems are described variously in U.S. Pat. Nos. 4,215,011; 4,232,177; 4,242,530; 4,302,356; 4,307,254; 4,336,407; 4,439,350; 4,443,559; and 4,482,775. U.S. Pat. No. 4,447,668 discloses the dissociation of ethers in a catalytic distillation column.

U.S. Pat. No. 3,267,156 discloses the preparation of dialkyl ethers by dehydration over acid resin catalyst at 250 to 400° F.

U.S. Pat. No. 4,827,048 discloses the production of MTBE using heteropoly acid catalyst on an inert support to dehydrate methanol and tertiary butyl alcohol in a straight pass reaction at 120° F.+.

U.S. Pat. No. 4,918,244 disclosed MTBE production by reacting methanol and tertiary butyl alcohol in a rectification tower in a packed bed.

SUMMARY OF THE INVENTION

Briefly, the present invention is a process for the production of ether comprising the steps of:

(a) feeding a tertiary alcohol to a first distillation column reactor into a feed zone;

(b) concurrently in said first distillation column reactor (i) contacting said tertiary olefin with an acid ion exchange resin catalyst as a component in distillation structure in a distillation reaction zone at a temperature in the range of 165° to 200° F., preferably at 0 to 50 psig thereby dissociating said tertiary alcohol to the corresponding tertiary olefin and water, characterized in that sufficient water is maintained in said distillation reaction zone to inhibit the reaction of the tertiary olefin with itself to form dimers and (ii) separating said tertiary olefin and said water by fractional distillation;

(c) withdrawing said tertiary olefin from said first distillation column reactor as overheads;

(d) withdrawing said unreacted tertiary alcohol and water from said first distillation column reactor as bottoms;

(e) feeding said tertiary olefin to a second distillation column reactor into a feed zone; and (f) contacting said tertiary olefin diluted with an inert alkane in the mole ratio of 1:5 to 1:100 and a $C_1$ to $C_6$ alcohol feed with an acid ion exchange resin catalyst as a component in distillation structure in a distillation reaction zone thereby reacting at least a portion of said alcohol and said tertiary olefin to form a reaction mixture containing an alkyl tertiary alkyl ether, unreacted alcohol and unreacted tertiary olefin, and (ii) separating said alkyl tertiary alkyl ether and said unreacted alcohol from said unreacted tertiary olefin by fractional distillation.

The acid ion exchange resin catalyst is in such a form as to act as both the catalyst for the reaction and distillation structure for the fractional distillation. Suitable catalytic distillation structures are the catalyst containing cloth belts described above and disclosed U.S. Pat. Nos. 4,215,011; 4,302,356 and 4,443,559 which are incorporated by reference herein.

Briefly, a preferred and commercial catalyst structure described in the above patents comprises a cloth belt with a plurality of pockets spaced along the belt and containing particulate catalyst material, said cloth belt being wound in a helix about a spacing material such as stainless steel knitted mesh. These units are then disposed in the distillation column reactor. In addition, U.S. Pat. No. 4,250,052 discloses a variety of catalyst structures for this use and is incorporated herein.

The success of catalytic distillation lies in an understanding of the principles associated with distillation. Because the reaction is occurring concurrently with distillation, the initial reaction product is removed from the reaction zone as quickly as it is formed which minimizes further reaction. The heat of the reaction, if any, simply creates more boil up, but no increase in temperature.

DESCRIPTION OF THE PREFERRED EMBODIMENT

1. Catalyst and Distillation Structure

Figure 1:
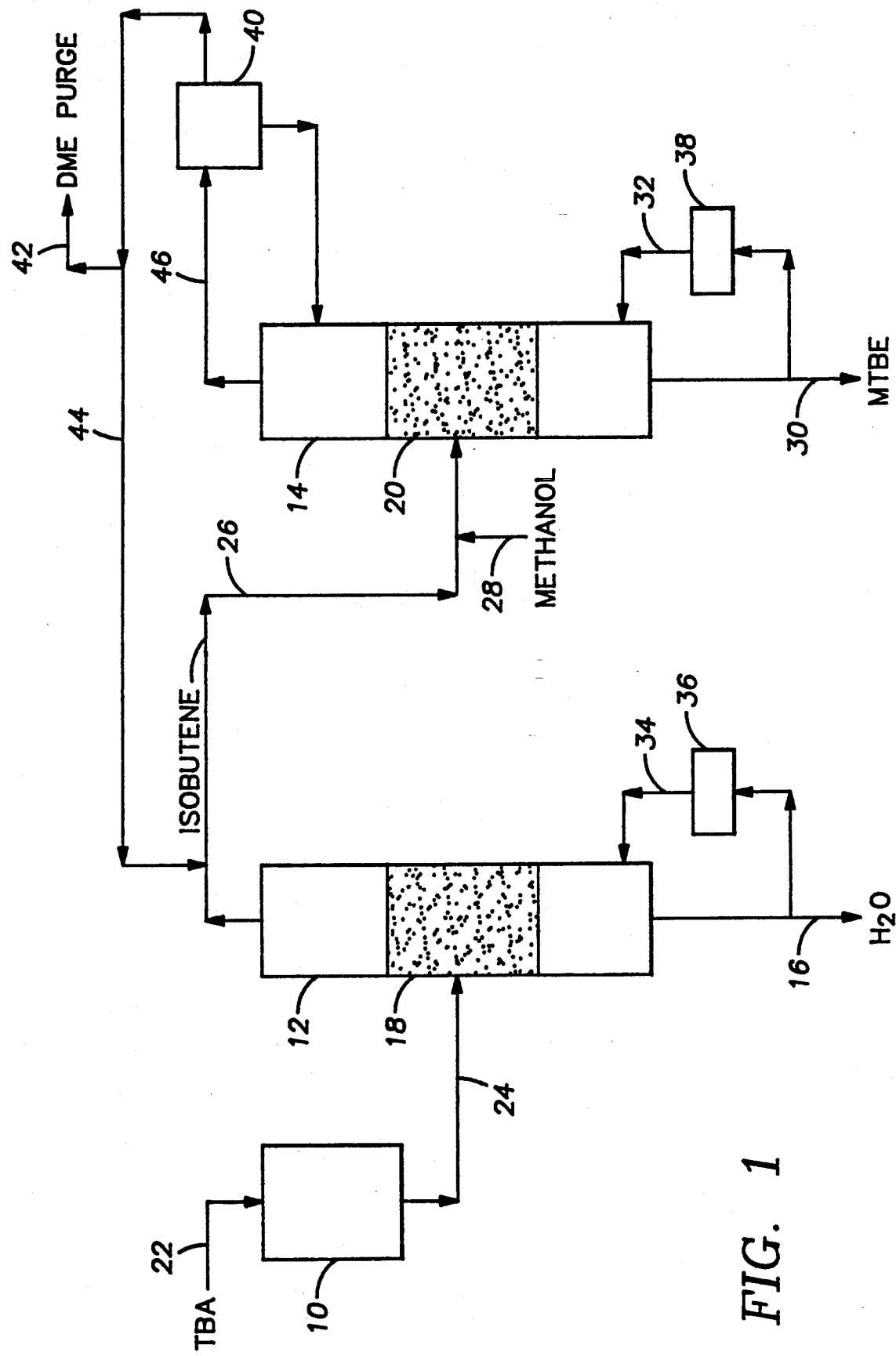
FIG. 1 is a flow diagram in schematic form of one embodiment of the present invention.

Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by cross-linking with polyvinyl compounds; for example, with divinyl benzene, divinyl toluene, divinyl phenylether and others The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification 908,240). The ion exchange resin is generally used in a granular size of about 0.25 to 1 mm, although particles from 0.15 mm up to about 2 mm may be employed. The finer catalysts provide high surface area, but also result in high pressure drops through the reactor. The macroreticular form of these catalysts have much larger surface area exposed and limited swelling which all of these resins undergo in a non-aqueous hydrocarbon medium compared to the gelular catalysts.

The container employed to hold the catalyst particles may have any configuration, such as the pockets disclosed in the patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus, desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like, each such larger component may be individually intimately associated with or surrounded by the spacing component as described above.

It is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred.

In the following examples the catalyst packing consisted of bags in the form of a fiber glass cloth belt approximately six inches wide with narrow pockets approximately ⅜ inch wide sewn across the belt. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the catalyst filled cloth pockets and provide a passage for vapor flow.

The wire mesh provides the support for the catalyst belt and provides some degree of vapor passage through the catalyst particles, which otherwise form a very compact bed which has a high pressure drop. Thus, the down flowing liquid is in intimate contact with the rising vapors and the catalyst in the column.

Catalyst packing may be made up of alternating layers of catalyst filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing could be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

2. Process Description

The reaction system can be described as heterogeneous since the catalyst remains as a distinct entity.

Bulk type liquid phase reactions have as one problem the control of the temperature. The distillation avoids the problem entirely. Because the reaction is occurring concurrently with distillation, the initial reaction products are removed from the reaction zone nearly as quickly as they are formed. The removal of olefin, e.g. isobutene, from the dehydration is important because the newly formed isoolefin has a tendency to react with itself in the presence of acid catalyst to form oligomers, in particular dimers. Similarly the removal of the ether, e.g. MTBE, from its reaction with alcohol, e.g. methanol, is of particular importance because it minimizes decomposition of the MTBE which is catalyzed by the same catalyst.

The tendency of isobutene to react with itself in the dehydration column is inhibited by maintaining sufficient water in that column to keep the catalyst wetted and also by operating the dissociation at lower temperatures than the prior art would normally use for a dehydration.

Also in the distillation column reactor because the mixture is boiling, the temperature of the reaction is controlled by the boiling point of the mixture in the reactor at the system pressure. The heat of the reaction, which is exothermic, simply consumes more boil up, but no change in temperature. That is, if the heat is added in excess, there is no harm done since the excess will only result in more boil up. Third, the reaction has an increased driving force because the reaction products have been removed and cannot contribute to the reverse reaction (Le Chatelier's Principle). Thus, a great deal of control over the rate of reaction and distribution of products can be achieved by regulating the system pressure. Also, adjusting the throughput (residence time = liquid hourly space velocity$^{-1}$) gives further control of product distribution.

The same analysis applies to the dehydration column, except that the temperature is kept lower than expected, since the dehydration is favored by higher temperatures, however these same higher temperatures also favor oligomerization. It has been found however that to inhibit the oligomerization, the catalyst is preferably maintained "wet". That is, the conditions of operation are such as to keep a portion of the water produced in the dehydration in the catalyst zone. Under these conditions the lower boiling alcohol-water azeotropes can be kept in the catalyst zone with none going out in the bottoms, thus producing essentially 100% conversion of the alcohol. For the preferred alcohols the conditions can be maintained with temperatures in the range of 165° to 175° F. and pressure in the first column is preferably in the range of 0 to 35 psig. Thus operating in these ranges, one maintains a portion of the water produced in the dehydration in the catalyst zone to keep the catalyst wet.

A reflux is preferably included in each distillation column reactor. The reflux ratio could vary over the rate of 0.5 to 25:1. In practice, the higher ratio may be used to compensate for a short catalyst bed such as required for experimental work. In commercial size units the catalyst bed would be provided so that lower reflux and hence higher unit productivity could be obtained, e.g., 0.5 to 2:1.

Preferred tertiary alcohols include tertiary butyl alcohol (TBA) and tertiary amyl alcohol (TAA). Hence the corresponding tertiary olefins from the dehydration are isobutene and isoamylene or mixtures thereof. The alcohol reactants may be the $C_1$ to $C_6$ monohydric alcohols, but are preferably methanol and ethanol or mixtures thereof. Hence the resulting ether products from the second distillation column reactor are preferably methyl tertiary butyl ether (isobutene+methanol), ethyl tertiary butyl ether (isobutene+ethanol), tertiary amyl methyl ether (methanol+isoamylene) and tertiary amyl ethyl ether (ethanol+isoamylene) or mixtures of these ethers.

The procedures for carrying out etherifcations in distillation column reactors is well described in the art and in particular U.S. Pat. Nos. 4,307,254 and 4,336,407 of Lawrence A. Smith, Jr. which are both incorporated herein in there entirety.

The isobutene feed produced from the present dehydration in highly concentrated, i.e., 90 mole % + isoolefin. This highly concentrated isoolefin feed is best not be directly employed in the etherification as described above in the cited patents. The isoolefin product must be diluted to the ranges of isoolefin which will best operate in catalytic distillation, e.g. up to about 70% isoolefin or more preferably a molar ratio of isoolefin: diluent of 1:5 to 1:100. The diluent may be the corresponding alkanes or different alkanes such that the resultant either is easily separated from the diluent in the distillation reactor column.

Alternatively the procedure described in commonly owned U.S. Pat. No. 5,118,873 which is incorporated herein in its entirety may be used.

Briefly the process described in that application is a process for etherification of substantially pure $iC_4=$ with MeOH to form MTBE in a distillation column reactor containing a fixed bed acid cation exchange resin as a catalytic distillation structure in an a distillation reaction zone. An inert $C_4$ hydrocarbon is initially fed to the distillation column reactor to act as a diluent and a heat sink which boils at the desired temperature range for the reaction. Additionally the inert $C_4$ diluent acts as an azeotroping agent for the MeOH in the lower end of the column carrying more of the MeOH back up into the reaction distillation zone. After start up and circulation the inert $C_4$ hydrocarbon feed is stopped and that in the system is retained therein by total reflux of the overheads and judicious operation of the lower portion of the distillation column reactor. Thus forming an isobutane blanket in the reactor. Very little, if any, of the inert $C_4$ hydrocarbon is taken as bottoms which primarily consists of the MTBE product and some unreacted MeOH. Some of the overheads may have to be withdrawn as a bleed stream to remove the lighter hydrocarbons which may be contained in the inert stream and for pressure control of the distillation column reactor. Preferably the mole ratio of isobutene to isobutane maintained in the catalyst zone is in the range of about 1:5 to 1:100 ; preferably 1:10 to 1:50. Make up inert $C_4$ hydrocarbon is added only to replace the small amount in the bottoms and the overhead bleed.

Referring now to the FIG. 1 a typical flow scheme is shown in simplified schematic form. For the purpose of this illustration the alcohol is tertiary butyl alcohol (TBA) which is fed via 22 to preheater 10 hence via 24 into distillation column reactor 12 in to the catalyst 18 prepared as described as distillation structures. The pressure is kept at about 0 psig thus keeping the temperature in the range of about 165° to 180° F. depending on the specific composition of the mixture in the column, with the temperature being higher in the bottoms because of the heavier materials there. The only bottoms 16 removed are substantially water, thus the TBA is conversion is 100%. A portion is recycled through reboiler 36 and 34.

The overheads 26 are primarily isobutene and any other lights, such as isobutane, which pass via 26 in to distillation column reactor 14 having been nixed with methanol added via 28. This admixture enters the catalyst 20 also prepared as a distillation structure where the reaction of isobutene and methanol produces MTBE. The MTBE is recovered as the bottoms 30 from column 14. A portion is recycled through reboiler 38 and 32.

The overheads 46 comprise any of the unreacted isobutene or other lights and a diluent such as isobutane, which pass through condenser 40 where a portion are condensed for return to column 14 as reflux. The remaining overheads are recycled 44 to the feed to column 14, except for small purge which serves to limit the dimethyl ether (DME) build up in the system.

EXAMPLE 1-3

The dehydration of TBA was carried out in a one inch automated distillation column reactor. The catalyst used was DOW M-31 cation exchange resin manufactured by Dow Chemical Co. and was placed into the cloth bags and supported as hereinabove described. Thirty-five feet of the catalyst were placed into the dehydration column with 2 feet of standard distillation packing above and 2 feet below the catalyst.

In example 1 410 ml of TBA was placed in the bottom of the tower. Distillation started at 1 atmosphere pressure. Isobutene was evolved overhead at about 15,000 ml/hour and shut down after 6 hours. Examples 2 and 3 were carried out by the same general procedure. Complete results along with conditions and flow rates for all examples are given in the TABLE.

TABLE

|  | EXAMPLE | | |
| --- | --- | --- | --- |
|  | 1 | 2 | 3 |
| Feed | 410 ml TBA | 400 ml TBA | 350 ml TBA |
| CONDITIONS | | | |
| Overhead Pressure | 1 atm | 50 psig | 80 psig |
| Bottom Temp, °F. | 175 | 255 | 275 |
| Catalyst Zone Temp, °F. | 170 | about 200 | 230-245 |
| Overhead Temp, °F. | N/A | about 80 | 120 |
| Product. Rate, OH vapor | 250 ml/min | 733 ml/min | 1.9 ml/min |
| ANALYSIS, wt % | OH    BTM* | OH    BTM | OH    BTM |
| Isobutane | 1.07 | | |
| N-Butane | 0.09 | | |
| Butene-1 | 0.05 | | |
| Isobutene | 98.70 | 100.00 | 99+ |
| Trans butene-2 | 0.09 | | |
| Cis butene-2 | | LE 0.42 | >10% DIB AND |
|  | | TBA 99.22 | OLIGOMERS IN |
|  | | DIB 0.063 | TBA + $H_2O$ |
|  | | UNK 0.29 | |

*not analyzed

The invention claimed is:

1. A two stage process for the production of ether comprising the steps of:
   (a) feeding a tertiary alcohol to a first distillation column reactor into a feed zone;
   (b) concurrently in said first distillation column reactor
      (i) contacting said tertiary alcohol with an acid ion exchange resin catalyst as a component in distillation structure in a distillation reaction zone at a temperature in the range of 165° to 200° F. thereby dissociating said tertiary alcohol to the corresponding tertiary olefin and water, characterized in that sufficient water is maintained in said distillation reaction zone to inhibit the reaction of the tertiary olefin with itself to form dimers and
      (ii) separating said tertiary olefin and said water by fractional distillation;
   (c) withdrawing said tertiary olefin from said first distillation column reactor as overheads;
   (d) withdrawing said unreacted tertiary alcohol and water from said first distillation column reactor as bottoms;
   (e) feeding said tertiary olefin to a second distillation column reactor into a feed zone; and
   (f) concurrently in said second distillation column reactor
      (i) contacting said tertiary olefin diluted with an inert alkane in the mole ratio of 1:5 to 1:100 and a $C_1$ to $C_6$ alcohol feed with an acid ion exchange resin catalyst as a component in distillation structure in a distillation reaction zone thereby reacting at least a portion of said alcohol and said tertiary olefin to form a reaction mixture containing an alkyl tertiary alkyl ether, unreacted alcohol and unreacted tertiary olefin, and
      (ii) separating said alkyl tertiary alkyl ether and said unreacted alcohol from said unreacted tertiary olefin by fractional distillation.

2. The process according to claim 1 wherein the overhead pressure in said first distillation column reactor is between 0 and 50 psig.

3. The process according to claim 2 wherein the temperature in the first distillation column reactor is in the range of 165° to 175° F.

4. The process according to claim 1 wherein said tertiary alcohol is tertiary butyl alcohol, isoamyl alcohol or mixtures thereof.

5. The process according to claim 1 wherein said tertiary alcohol is isoamyl alcohol.

6. The process according to claim 5 wherein the overhead pressure in said first distillation column reactor is between 15 and 50 psig.

7. The process according to claim 3 wherein said tertiary alcohol is tertiary butyl alcohol.

8. The process according to claim 1 wherein the alcohol feed to the second distillation column reactor is methanol, ethanol or a mixture thereof.

9. The process according to claim 5 wherein the alcohol feed to the second distillation column reactor is methanol, ethanol or a mixture thereof.

10. The process according to claim 7 wherein the alcohol feed to the second distillation column reactor is methanol, ethanol or a mixture thereof.

11. A process for the production of isoolefin comprising the steps of:
    (a) feeding tertiary alcohol to a distillation column reactor into a feed zone;
    (b) concurrently in said distillation column reactor
       (i) contacting said tertiary alcohol with an acid ion exchange resin catalyst as a component in distillation structure in a distillation reaction zone at a temperature in the range of 165° to 200° F. thereby dissociating said tertiary alcohol to the isoolefin and water, characterized in that sufficient water is maintained in said distillation reaction zone to inhibit the reaction of the isoolefin with itself to form dimers and (ii) separating said isoolefin and said water by fractional distillation;

(c) withdrawing said isoolefin from said distillation column reactor as overheads; and (d) withdrawing said unreacted tertiary alcohol and water from said distillation column reactor as bottoms.

12. The process according to claim 11 wherein the overhead pressure in the distillation column reactor is in the range of 0 to 50 psig.

13. The process according to claim 12 wherein the overhead pressure in the distillation column reactor is in the range of 0 to 35 psig.

14. The process according to claim 13 wherein the temperature in the distillation column reactor is in the range of 165° to 175° F.

15. The process according to claim 14 wherein the tertiary alcohol comprises tertiary butyl alcohol and the isoolefin comprises isobutene.

16. The process according to claim 14 wherein the tertiary alcohol comprises isoamyl alcohol and the isoolefin comprises isoamylene.

* * * * *